United States Patent [19]

Rancurel

[11] Patent Number: 5,262,163
[45] Date of Patent: Nov. 16, 1993

[54] PROCESS FOR PREPARING THE NONSAPONIFIABLE MATTER OF AVOCADO ENABLING IN ONE OF ITS FRACTIONS TERMED H TO BE IMPROVED

[75] Inventor: Alain Rancurel, Mainvilliers, France

[73] Assignee: Laboratoires Pharmascience, Courbevoie, France

[21] Appl. No.: 759,268

[22] Filed: Sep. 13, 1991

[30] Foreign Application Priority Data

Jul. 3, 1991 [FR] France ............... 91 08301

[51] Int. Cl.$^5$ ............... A61K 35/78; A23D 9/00
[52] U.S. Cl. ............... 424/195.1; 426/417; 426/489; 426/492
[58] Field of Search ............... 424/195.1; 426/417, 426/489, 492

[56] References Cited

U.S. PATENT DOCUMENTS

| | | | |
|---|---|---|---|
| 2,550,254 | 4/1951 | Jensen | 424/195.1 |
| 4,560,568 | 12/1985 | Curiel | 426/417 |
| 4,793,990 | 12/1988 | Grollier | 424/59 |
| 4,944,954 | 7/1990 | Strop | 426/417 |
| 4,963,346 | 10/1990 | Amer | 424/49 |

Primary Examiner—Michael G. Wityshyn
Assistant Examiner—Ralph Gitomer
Attorney, Agent, or Firm—Skjerven, Morrill, MacPherson, Franklin & Friel

[57] ABSTRACT

The invention relates to a process for preparing the nonsaponifiable matter of avocado oil from the fruit, wherein the nonsaponifiable matter of avocado oil is separated and its content in one of its fractions termed H is improved by carrying out the heat treatment of the fruit before extracting the oil at a temperature of 80° C. to 120° C. for not less than four hours.

It also relates to the nonsaponifiable matter obtained by the process and to medicinal products, cosmetics and food additives containing it.

7 Claims, No Drawings

PROCESS FOR PREPARING THE NONSAPONIFIABLE MATTER OF AVOCADO ENABLING IN ONE OF ITS FRACTIONS TERMED H TO BE IMPROVED

The subject of the invention is in particular a process for preparing the nonsaponifiable matter of avocado oil from the fruit enabling its content in one of the fractions termed H to be improved.

It has in effect been noted that the quality of the nonsaponifiable matter obtained may vary as a function of certain treatments, in particular of the raw material. Accordingly, in order to obtain a nonsaponifiable matter of avocados rich in fraction H, the Applicant Company has developed the process which is the subject of the present invention.

Fraction H is that which:

migrates in front with an Rf of 0.9 in thin-layer chromatography, is eluted first in high performance liquid chromatography on silica, appears preponderantly in gas phase chromatography.

In the process according to the invention, the nonsaponifiable matter is separated from the avocado oil and the quality of this nonsaponifiable matter is improved by carrying out the heat treatment of the fruit before extracting the oil at a temperature of 80° C. to 120° C. for not less than four hours, advantageously not less than 10 hours and preferably for 24 to 48 hours.

Given its corrective properties of some connective tissue disorders such as those of the skin or periodontium, articulatory cartilage and the like), the non-saponifiable matter thus obtained may be used as active ingredient in the pharmaceutical, cosmetic or food industries, in particular to prevent the onset of skin ageing, of arthritis or of paradontopathies. Used regularly, this nonsaponifiable matter definitely provides comfort in the elderly in particular.

The nonsaponifiable matter is the fraction of a fatty substance which after prolonged action of an alkaline base, remains insoluble in water and may be extracted with an organic solvent. Five main groups of substances are present in most vegetable nonsaponifiable matter: saturated or unsaturated hydrocarbons, aliphatic or terpene alcohols, sterols, tocopherols and carotenoid and xanthophyllic pigments.

Comparison of the nonsaponifiable matter contents of various vegetable oils: soya bean, cotton, coconut, olive and avocado show a very high level of nonsaponifiable matter in avocado oil obtained by extraction using various processes including that of the invention. Typically, the contents obtained range from 2 to 7% of nonsaponifiable matter in avocado oil compared to 0.5% in coconut oil, 1% in soya bean oil and 1% in olive oil. This substantial difference is due to the presence, in the nonsaponifiable matter of avocado, of constituents which are not generally found in the nonsaponifiable matter of numerous other vegetable oils and which, alone, represent more than 50% of the nonsaponifiable matter.

Avocado oil is obtained from the fruit using various methods:

either the fresh pulp is pressed in the presence of a third water-absorbing fibrous substance such as coffee parchment in a cage press or in an oil-bag press and then the oil-and-water emulsion obtained is separated by decantation or centrifugation, or the fresh pulp is crushed and brought into contact with a suitable solvent such as a methanol/chloroform mixture, the solvent phase is recovered and evaporated, or finally, by drying the fruits beforehand before extracting them using a solvent or pressing them according to processes known to a person skilled in the art.

The oil thus obtained contains triglycerides on the one hand and the nonsaponifiable fraction on the other hand.

Several processes hove been described for extracting the nonsaponifiable matter of a vegetable oil. All of them involve saponification using potassium hydroxide or sodium hydroxide in ethanolic medium, followed by one or more extractions either with petroleum ether or with ethyl ether, or with any other suitable solvent immiscible with the water-alcohol solution.

However, the preceding operation, as its name indicates, results in the complete loss of triglycerides. That is why it is endeavoured where possible to partly recover the triglycerides by concentrating the nonsaponifiable matter beforehand. Various methods may be used: low-temperature crystallization, liquid-liquid extraction, molecular distillation and steam distillation. Molecular distillation or partial molecular distillation of the oil has numerous advantages.

After this preliminary treatment, the concentrate or distillate previously obtained is saponified in a known manner. The nonsaponifiable matter is then extracted with a suitable solvent. The solution obtained is washed with water to eliminate residual traces of alkalinity. Finally, the solvent is carefully evaporated in order to recover the nonsaponifiable matter.

The preliminary heat treatment according to the present invention, makes it possible to obtain a fraction H-rich nonsaponifiable matter, compared to that obtained by the conventional process, namely dehydration of the fruit, extraction of the oil and extraction of the nonsaponifiable matter. Thus, the fruit dehydrated by freeze-drying results in a nonsaponifiable matter free of fraction H.

According to the invention, the fruit oil, previously dehydrated and heat treated, preferably for not less than 4 hours, advantageously 10 hours, at a temperature of 80°-120° C., or dehydrated and heat treated in combination may have between 30 and 60% of nonsaponifiable matter consisting of fraction H.

As stated, the heat treatment may be preceded by dehydration of the fruit, but preferably, the dehydration is achieved during the heat treatment.

The subject of the invention is also the nonsaponifiable matter of avocado obtained by the process described above.

Generally, for 100 g of fresh pulp, between 0.1 g and 1 g of nonsaponifiable matter is obtained on average.

Given that the nonsaponifiable matter aims to maintain good functioning of bone cartilages, in particular for people of a certain age, it may be useful to prepare it in the form of a food additive to be consumed either alone or introduced in a food preparation.

The process for preparing the nonsaponifiable matter is illustrated by the following example:

EXAMPLE 1

Preparation of the nonsaponifiable matter 160 g of avocado cut into sections about 5 mm thick are subjected to the following operations:

A—Drying and heat treatment

The sliced fruits are placed in an oven regulated at 80° C. for 24 hours, they are then crushed.

B—Extraction

The powder obtained in the preceding stage is extracted.

The cake is removed and the hexane solution is evaporated under reduced pressure.

20 g of avocado oil are obtained.

C—Molecular distillation

In the method chosen, the oil is spread out in a thin layer on the heated surface of a conical rotor revolving at high speed. A high vacuum, of the order of $10^{-3}$ mm Hg, is maintained in the distillation chamber.

Under these conditions, there is evaporation and not boiling, from the hot surface, of the constituents of the nonsaponifiable matter whose separation becomes possible with respect to the glycerides, the advantage being that the oil and the nonsaponifiable matter (these products being reputed unstable) are not degraded during the evaporation. The distillation temperatures are of the order of 180° to 230° C. The concentration of nonsaponifiable matter in the distillate may be as high as 60%. The concentrate obtained is then treated using the process already described.

D—Saponification 50 g of the oil obtained in Stage B are mixed with 25 ml of 12 N potassium hydroxide and 100 ml of ethanol and refluxed for 4 hours.

175 ml of water are added to the water-alcohol phase, 175 ml of dichloroethane are then added and stirred and then allowed to settle; the organic phase is then recovered; this operation is repeated 5 to 6 times. The organic phases are combined, washed with water and the solvent evaporated, 2 g of nonsaponifiable matter are thus obtained. For an industrial preparation, the extraction stages in flasks may be advantageously replaced by a continuous extraction in a continuous liquid-liquid extraction apparatus such as a pulsed column, a mixer-settler or their equivalents.

COMPARATIVE TEST

Avocados cut into sections about 5 mm thick are subjected to a freeze-drying operation. The dried fruit is extracted in the same manner as in Stage B of Example 1. The oil obtained is purified for analysis by thin-layer chromatography (elution with hexane). No trace of fraction H was detected during this analysis.

I claim:

1. A process for preparing nonsaponifiable matter of avocado oil extracted from avocado fruit wherein the content of one of the fractions termed H of said oil is increased, comprising:

heat treating the fruit at a temperature of 80 degrees C. to 120 degrees C. for not less than four hours before extracting the oil; and separating the nonsaponifiable matter from the avocado oil.

2. The process as claimed in claim 1, wherein the heat treatment lasts for not less than 10 hours.

3. The process as claimed in claim 1, wherein the separation of the nonsaponifiable matter from the oil is carried out by molecular distillation of the nonsaponifiable matter to form a distillate, and then by saponification of the distillate obtained.

4. The process as claimed in claim 1, wherein the heat treatment is preceded by dehydration of the fruit.

5. The process as claimed in claim 4, wherein the dehydration is achieved during the heat treatment.

6. The process as claimed in claim 5, wherein the heat treatment lasts for not less than 10 hours.

7. A nonsaponifiable fraction of avocado oil containing 30-60% of fraction H, obtained as claimed in the process of any of claim 1-6.

* * * * *